United States Patent
Huang et al.

(10) Patent No.: US 8,431,060 B2
(45) Date of Patent: Apr. 30, 2013

(54) METHOD OF FABRICATING AN IMPLANTABLE MEDICAL DEVICE USING GEL EXTRUSION AND CHARGE INDUCED ORIENTATION

(75) Inventors: Bin Huang, Pleasanton, CA (US); David C. Gale, Kennesaw, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 291 days.

(21) Appl. No.: 12/559,404

(22) Filed: Sep. 14, 2009

(65) Prior Publication Data

US 2010/0096781 A1  Apr. 22, 2010

Related U.S. Application Data

(63) Continuation-in-part of application No. 11/345,073, filed on Jan. 31, 2006, now abandoned.

(51) Int. Cl.
| | | |
|---|---|---|
| *B28B 1/24* | (2006.01) | |
| *B29C 55/12* | (2006.01) | |
| *A61F 2/04* | (2006.01) | |
| *A61F 2/82* | (2006.01) | |

(52) U.S. Cl.
USPC ........ 264/310; 264/290.2; 264/294; 264/309; 264/331.12; 523/113; 424/426

(58) Field of Classification Search .................. 264/310, 264/290.2, 294, 309, 331.12; 523/113; 424/426
See application file for complete search history.

(56) References Cited

U.S. PATENT DOCUMENTS

| | | | |
|---|---|---|---|
| 3,583,961 A | 6/1971 | Magay | |
| 3,674,628 A | 7/1972 | Fabre | |
| 4,044,404 A | 8/1977 | Martin et al. | |
| 4,436,689 A | 3/1984 | Smith et al. | |
| 4,668,717 A | 5/1987 | Lemstra et al. | |
| 7,144,632 B2 | 12/2006 | Hayes | |
| 2002/0081732 A1* | 6/2002 | Bowlin et al. ................. | 435/446 |
| 2003/0083732 A1 | 5/2003 | Stinson | |
| 2004/0156904 A1* | 8/2004 | Saltman et al. ................ | 424/486 |
| 2006/0085063 A1 | 4/2006 | Shastri et al. | |
| 2006/0165754 A1* | 7/2006 | Ranade ......................... | 424/423 |
| 2007/0007688 A1 | 1/2007 | Kristiansen et al. | |
| 2007/0158880 A1 | 7/2007 | Dave | |
| 2007/0168011 A1* | 7/2007 | LaDuca et al. ................ | 623/1.11 |
| 2007/0269481 A1* | 11/2007 | Li et al. ........................ | 424/423 |

FOREIGN PATENT DOCUMENTS

| | | |
|---|---|---|
| EP | 0 770 401 | 5/1997 |
| GB | 1 530 990 | 11/1978 |

OTHER PUBLICATIONS

International Search Report for PCT/US2006/049297, filed Dec. 22, 2006, mailed Jun. 1, 2007, 10 pgs.

* cited by examiner

*Primary Examiner* — Tae H Yoon
(74) *Attorney, Agent, or Firm* — Squire Sanders (US) LLP

(57) ABSTRACT

The invention provides a method of manufacturing a polymeric implantable medical device using gel extrusion of high molecular weight polymers or charge-induced orientation to avoid heat degradation of the polymer that might occur during conventional heat extrusion.

16 Claims, 3 Drawing Sheets

METHOD OF FABRICATING AN IMPLANTABLE MEDICAL DEVICE USING GEL EXTRUSION AND CHARGE INDUCED ORIENTATION

RELATED APPLICATIONS

This application is a continuation-in-part of application Ser. No. 11/345,073, filed 31 Jan. 2006, now abandoned, which is incorporated by reference, including any drawings, as if fully set forth herein.

FIELD

This invention relates to methods of fabricating implantable medical devices. More particularly it relates to gel extrusion and charge induced orientation techniques to accomplish the goal so as to reduce or eliminate decomposition of polymers due to heat during conventional melt extrusion.

BACKGROUND

This invention relates to medical devices adapted to be implanted in a bodily lumen. A "lumen" refers to a cavity of a tubular organ such as a blood vessel. A stent is an example of an implantable medical device. Stents are generally cylindrically shaped devices which function to hold open and sometimes expand a segment of an anatomical lumen such as, for instance, a blood vessel, urinary tract or bile duct. Stents are often used in the treatment of atherosclerotic stenosis in blood vessels. "Stenosis" refers to a narrowing or constriction of the diameter of a lumen. In such treatments, stents reinforce the vessel and serve to reduce the incidence of restenosis following angioplasty. "Restenosis" refers to the reoccurrence of stenosis in a blood vessel or heart valve after it has been treated as by balloon angioplasty or valvuloplasty.

Stents have been made of many materials including metals and polymers. Polymer materials include both biostable and biodegradable polymers. The cylindrical structure of stents is typically composed of scaffolding that includes a pattern of interconnecting structural elements. The scaffolding can be formed from wires, tubes, or planar sheets of material rolled into a cylindrical shape. A stent may be medicated by coating the surface the scaffolding with a polymeric carrier that contains an active agent or drug. Generally, the pattern of the scaffolding allows the stent to be radially expandable and to be longitudinally flexible.

Longitudinal flexibility facilitates delivery of the stent and lateral rigidity is needed to hold open a bodily lumen. The pattern should be designed to maintain the longitudinal flexibility and rigidity required of the stent.

A number of techniques have been suggested for the fabrication of stents from tubes and planar films or sheets. One such technique involves laser cutting or etching a pattern into a material. Laser cutting may be performed on a planar sheet of a material which is then rolled into a tube. Alternatively, a desired pattern may be etched directly onto a tube. Other techniques involve cutting a desired pattern into a sheet or a tube via chemical etching or electrical discharge machining. Laser cutting of stents has been described in a number of publications including U.S. Pat. No. 5,780,807 to Saunders, U.S. Pat. No. 5,922,005 to Richter, and U.S. Pat. No. 5,906,759 to Richter.

A stent must be delivered and deployed. "Delivery" refers to introducing and transporting the stent through a bodily lumen to a region requiring treatment. "Deployment" refers to the expanding of the stent within the lumen at the treatment region. Delivery and deployment of a stent are accomplished by positioning the stent at one end of a catheter, inserting the end of the catheter through the skin into a bodily lumen, advancing the catheter to the desired treatment location, expanding the stent at the treatment location and removing the catheter. In the case of a balloon expandable stent, the stent is mounted about a balloon disposed on the catheter. Mounting the stent typically involves compressing or crimping the stent onto the balloon. Once delivered to the treatment location, the stent is expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn allowing the stent to self-expand.

Some treatments with implantable medical devices require the presence of the device only for a limited period of time. Once treatment is complete, which may include structural tissue support and/or drug delivery, it may be desirable for the stent to be removed from the treatment location. One way of removing a stent is by fabricating at least part of the device from materials that erode or disintegrate when exposed to conditions within the body. Thus, erodible portions of the device can disappear or substantially disappear from the implant region after the treatment regimen is completed. After the process of disintegration is completed, desirably no portion of the device will remain although in some cases negligible traces of residue may be observed.

The terms degrade, absorb, resorb, erode and the normal English language versions of these words are used interchangeably and refer to materials that are capable of being substantially completely, preferably completely, desintegrated when exposed to bodily conditions and thereafter being resorbed, absorbed, and/or eliminated by the body.

A potential shortcoming of implantable medical devices made from polymer material compared to metal stents is that polymer stents typically have less circumferential strength and rigidity. Inadequate circumferential strength may result in relatively high recoil of such polymeric devices after implantation into vessels. Furthermore, struts of polymer devices can crack during crimping, especially if the polymer is brittle. Therefore, methods of manufacturing polymer devices that improve circumferential strength and rigidity are desirable.

SUMMARY

Thus, in one aspect the present invention relates to a method of manufacturing an implantable medical device, the method comprising:

a. Dissolving a matrix polymer having a number average molecular weight of at least 100,000 Da in a first solvent at a concentration such that a gel is formed;

b. Extruding the gel through an extrusion apparatus to form a tube or a sheet;

c. Quenching the formed tube or sheet in a second solvent that does not dissolve the matrix polymer but which allows the first solvent to diffuse out of the polymer;

d. Drying the tubing or sheet; and e. Forming the implantable medical device from the dried tubing or sheet.

In an aspect of this invention, the formed tube is radially expanded after quenching and prior to drying.

In an aspect of this invention, the radially expanded tubing is axially oriented after quenching and prior to drying.

In an aspect of this invention, the tube is axially oriented by stretching it to at least about 20 times its initial length.

In an aspect of this invention, the formed sheet is biaxially oriented after quenching and prior to drying.

In an aspect of this invention, the implantable medical device is a stent.

In an aspect of this invention the matrix polymer has a number average molecular weight of at least about 500,000 Da.

In an aspect of this invention, the matrix polymer has a number average molecular weight of at least about 1,000,000.

In an aspect of this invention, the matrix polymer is selected from the group consisting of Poly(D,L-lactide); poly (L-lactide); poly(L-lactide-co-glycolide); poly (D,L-lactide-co-glycolide); chitin; chitosan; any copolymers thereof, and any mixtures thereof in any proportion.

In an aspect of this invention, the concentration of the polymer in the solvent is about 0.1 percent (w/w) to about 20% percent (w/w).

In an aspect of this invention, the gel in the extrusion apparatus is at a temperature at which there is no or substantially no molecular weight degradation.

In an aspect of this invention, the temperature of the gel in the extrusion apparatus is about room temperature.

In an aspect of this invention, after forming the tubing or sheet from the polymer gel and drying the tube or sheet, the average molecular weight of the matrix polymer is greater than about 90% of its molecular weight prior to extrusion.

An aspect of this invention relates to a method of manufacturing an implantable medical device, the method comprising:
 a. disposing a polymer fluid comprising a solvent and a matrix polymer into a forming apparatus;
 b. inducing a charge in the polymer fluid, wherein the charge induces orientation of polymer chains in the polymer fluid;
 c. forming a polymeric sheet with the induced orientation from the charged polymer fluid;
 d. depositing the polymeric sheet onto a rotating cylindrical member to form a polymeric tube with the induced orientation over the rotating cylindrical member; and
 e. fabricating an implantable medical device from the polymeric tube.

In an aspect of this invention, the implantable medical device is a stent.

In an aspect of this invention, the forming apparatus is selected from the group consisting of a die, an extruder, or a combination thereof.

In an aspect of this invention, the temperature of the polymer fluid in the forming apparatus is at or about room temperature.

In an aspect of this invention, at least a portion of the formed polymeric sheet comprises a gel.

In an aspect of this invention, the polymeric tube is formed such that it comprises the induced orientation along a selected direction.

In an aspect of this invention, the polymeric sheet is deposited so that the polymeric tube comprises multiple layers.

In an aspect of this invention, the molecular weight of the polymer is at least about 100,000.

In an aspect of this invention, a relative concentration of the polymer and the solvent in the polymer fluid are such that the polymeric sheet substantially maintains its shape upon removal from the apparatus.

In an aspect of this invention, the method further comprises depositing fibers over the polymeric tube to form a cylindrical fiber layer over the polymeric tube.

As aspect of this invention relates to a method of manufacturing an implantable medical device, the method comprising:
 a. inducing a charge in the polymer fluid comprising a solvent and a matrix polymer with a molecular weight of at least about 100,000;
 b. spraying the charged polymer fluid to form a fluid jet;
 c. depositing fibers formed from the fluid jet over a rotating cylindrical member to form a cylindrical fiber layer; and
 d. forming an implantable medical device comprising the cylindrical fiber layer.

In an aspect of this invention, the implantable medical device is a stent.

In an aspect of this invention, the fiber layer is formed over a pre-formed polymer tube over the rotating cylindrical member.

In an aspect of this invention, the molecular weight of the polymer is at least about 500,000.

In an aspect of this invention, a plurality of the deposited fibers are aligned along a circumferential direction resulting from rotation of the rotating cylindrical member.

In an aspect of this invention, deposition of the fibers is facilitated by a potential difference.

DETAILED DESCRIPTION

Figure 1:
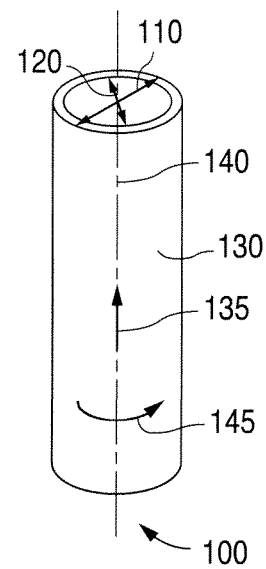
FIG. 1 depicts a tube.

For the purposes of the present invention, the following terms and definitions apply:

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis in testing which a material will withstand prior to fracture. The ultimate strength is calculated from the maximum load applied during the test divided by the original cross-sectional area.

"Modulus" may be defined as the ratio of the stress or force per unit area applied to a material divided by the amount of strain resulting form the applied force.

"Strain" refers to the amount of elongation or compression that occurs in a material at a given stress or load.

"Elongation" may be defined as the increase in length in a material which occurs when subjected to stress. It is typically expressed as a percentage of the original length.

"Solvent" is defined as a substance capable of dissolving or dispersing one or more other substances or capable of at least partially dissolving or dispersing the substance(s) to form a uniformly dispersed solution at the molecular- or ionic-size level. The solvent should be capable of dissolving at least 0.1 mg of the polymer in 1 ml of the solvent, and more narrowly 0.5 mg in 1 ml at ambient temperature and ambient pressure.

"Implantable medical device" is intended to include, but is not limited to, self-expandable stents, balloon-expandable stents, stent-grafts, and grafts. The structural pattern of the device can be of virtually any design. The device can also be made partially or completely from a biodegradable, bioabsorbable, or biostable polymer.

The "glass transition temperature," Tg, is the temperature at which the amorphous domains of a polymer change from a brittle vitreous state to a solid deformable state at atmospheric pressure. In other words, the Tg corresponds to the temperature where the onset of segmental motion in the polymer chains occurs. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Various embodiments of methods for manufacturing an implantable medical device with desirable mechanical properties are described herein. Some embodiments of manufacturing an implantable medical device, such as a stent, may include fabricating the implantable medical device from a polymer conduit or tube.

The tube may be cylindrical or substantially cylindrical in shape. For example, FIG. 1 depicts a tube 100. Tube 100 is a cylinder with an outside diameter 110 and an inside diameter 120. FIG. 1 also depicts a surface 130 and a cylindrical axis 140 of tube 100. When referred to below, unless otherwise specified, the "diameter" of the tube refers to the outside diameter of the tube. In some embodiments, the diameter of the tube prior to fabrication of the implantable medical device may be between about 0.5 mm and about 3.0 mm. In other embodiments, the diameter of the tube prior to fabrication may be between about 1 mm and 2 mm. An example of a tube prior to fabrication may include one with a diameter of 2.13 mm (0.084 in). A tube 100 can also be formed by rolling up and bonding a sheet or film. A polymeric tube or sheet may be formed by various methods, including, but not limited to extrusion or injection molding.

Figure 2:
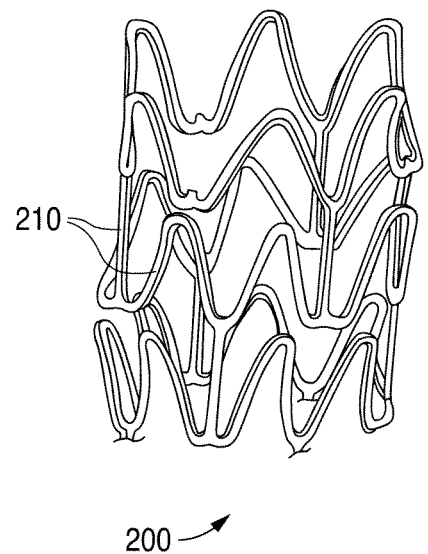
FIG. 2 depicts a three-dimensional stent.

In some embodiments, a stent may include a pattern or network of interconnecting structural elements or struts. FIG. 2 depicts a three-dimensional view of a stent 200 that may be formed from tube 100 in FIG. 1. Stent 200 includes a pattern of struts 210, which can take on a variety of patterns. The structural pattern of the device can be of virtually any design.

The embodiments disclosed herein are not limited to stents or to the stent pattern illustrated in FIG. 2. The embodiments are easily applicable to other patterns and other devices. The variations in the structure of patterns are virtually unlimited. As shown in FIG. 2, the geometry or shapes of stents vary throughout its structure. A stent such as stent 200 may be fabricated from a tube by forming a pattern with a technique such as laser cutting or chemical etching.

In other embodiments, an implantable medical device, such as a stent, can be fabricated in whole or in part from fibers and/or particles. A "fiber" may be defined as a unit of matter having a length substantially longer than its width or diameter. As used herein, a fiber can include, but is not limited to, a filament or a strip. In one embodiment, fiber or particles may be deposited on a surface of a polymeric matrix of a device or mixed, dispersed, or embedded within such polymeric matrix of a device, e.g., a tube or the structural elements of a strut. In certain embodiments, an implantable medical device, such as a stent, may be fabricated from a fiber layer that is a woven structure. A woven structure may refer to any structure produced from between one and several hundred or more fibers that are woven, braided, knitted, helically wound, and/or intertwined in any manner. Woven fibers in the shape of a tube may be disposed at angles between 0° and 180° degrees with the cylindrical axis of the tube, depending upon the overall geometry and dimensions desired.

In some embodiments, a polymeric fiber may be formed using any of a number of methods known in the art including, but not limited to, melt spinning, wet spinning, dry spinning, gel spinning, electrospinning, or an atomizing process. Fibers may be fabricated with relatively high polymer chain orientation along the fiber axis, and thus relatively high strength and stiffness.

A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes.

If a biodegradable polymeric material is used to coat the implantable medical device, it is understood that after the process of degradation, erosion, absorption, and/or resorption has been completed, no polymer will remain on the device. In some embodiments, very negligible traces or residue may be left behind. For stents made from a biodegradable polymer, the stent is intended to remain in the body for a period of time until its intended function, such as maintaining vascular patency and/or drug delivery, is accomplished.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide), poly(D,L-lactide), poly (caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

With regard to molecular weight of suitable polymers of this invention, any such designation is understood to refer to a number average molecular weight as such is understood by those skilled in the art. In brief, to determine a number average molecular weight refers to the ordinary arithmetic mean or average of the molecular weight of the individual macromolecules that make up the bulk polymer. It is measured by determining the molecular weight of n polymer molecules, summing the weights and dividing by n. The number average molecular weight can be determined by gel permeation chromatography, viscometry (using the Mark-Houwink equation) and various colligative methods including vapor pressure osmometry and end-group titration. These and any other methods known or as become known to those skilled in the art may be used to determine the number average molecular weight of a polymer of this invention.

As discussed above, a polymer tube or sheet for use in manufacturing an implantable medical device, such as a stent, should have adequate strength both in the longitudinal direction 135 and the circumferential direction 145 (FIG. 1). Biaxial molecular orientation, molecular orientation in both the longitudinal direction and the circumferential direction, increases the strength in the longitudinal and circumferential directions. The increased strength to weight ratio due to biaxial orientation allows fabrication a device with a similar strength and profile as a metallic device. Implantable medical devices, such as stents, fabricated from tubes or sheets with biaxial orientation may possess desired mechanical properties even with a sufficiently low profile structure, i.e., with a wall thickness and strut width. Several embodiments of manufacturing implantable medical devices with biaxial orientation, and hence, with desired mechanical properties are described herein.

It is generally known that as the molecular weight of a polymer increases, the mechanical strength and modulus increase. For this reason, it would be desirable to have an implantable medical device that is composed partially or completely of a relatively high molecular weight polymer. Relatively high molecular weight polymer polymers may include ultra high molecular weight ("UHMW") polymers which generally refer to polymers with a molecular weight greater than about 1,000,000 and are especially desirable for use in implantable medical devices. Relatively high molecular weight polymers may include polymers with a molecular weight greater than about 100,000; 300,000; 500,000; or more narrowly greater than 800,000.

Unfortunately, there tends to be an upper limit on the molecular weight of a polymer that can be used with conventional melt phase extrusion or injection molding processes. The higher the molecular weight of a polymer, the more difficult it is to extrude a shape such as a tube, sheet, or fiber with a melt phase process due to the high viscosity of the polymer. This is because the viscosity of a polymer melt increases with molecular weight. Thus, high molecular weight polymers require much higher extrusion temperatures to obtain a polymer with a viscosity that is low enough for extrusion. However, polymer molecules tend to undergo significant degradation at such high temperatures, resulting in a decrease in molecular weight. Therefore, molecular weight in the tubing, sheet, or fiber that is extruded through the melt phase tends to be low even if an ultra high molecular weight polymer is used.

In contrast to conventional melt phase extrusion, embodiments of the present invention advantageously allows for extrusion of an UHMW polymeric part, such as a tube, sheet, or fiber, at a relatively low temperature. The temperature may be at or below a temperature at which low or no degradation of the polymer occurs. For example, the temperature of the polymer fluid may be less than the polymer's melting temperature (Tm). The embodiments include extrusion of a polymer solution including a relatively high molecular weight polymer, such as an UHMW polymer. In this way, an implantable medical device may be formed from relatively high molecular weight polymers without substantially degrading the molecular weight of relatively high molecular weight polymers.

Rather than extruding a polymer melt, embodiments of the present invention involve extrusion of a polymer fluid that includes a polymer mixed with a solvent. The embodiments are similar to the process commonly known as "gel extrusion", also known as phase separation or extraction or wet process. In gel phase extrusion, the polymer fluid has a viscosity low enough to be extruded at temperatures below the melting point of the polymer. Consequently, the polymer fluid including a relatively high molecular weight polymer may be processed at relatively low temperatures at which there is no or substantially no molecular weight degradation. The substantial reduction or elimination of molecular weight degradation is especially advantageous in processing UHMW polymers.

Representative examples of solvents for use in the polymer fluid include chloroform, acetone, chlorobenzene, ethyl acetate, 1, 4-dioxane, ethylene dichloride, 2-ethyhexanol, and mixtures thereof. Other solvents can also be used to form the polymer fluid.

Mixing a solvent with the polymer effectively lowers the glass transition temperature of the polymer. The polymer chains in the polymer fluid have segmental and rotational mobility analogous to that of the polymer above its glass transition temperature and melting temperature. The increased segmental mobility allows for reduced processing temperature of the polymer. The reduced processing temperature is especially advantageous for processing UHMW polymeric parts, such as a tubes, sheets, or fibers, because molecular weight degradation of the UHMW polymer is reduced at lower processing temperatures.

Another advantage of the embodiments described herein is that processing a polymer-solvent mixture facilitates inducing biaxial orientation in a polymeric part such as a polymeric tube or polymeric sheet. Extrusion imparts large forces on the molecules in the longitudinal direction of the tube due to shear forces on a polymer or fluid being processed. The shear forces arise from forcing the polymer fluid through a die and pulling and forming the polymer fluid into the small dimensions of a tube or sheet, for example. As a result, a polymeric part formed by extrusion tends to possess a significant degree of longitudinal orientation.

Additionally, as described below, circumferential orientation may be induced through radial expansion of a formed tube. A high degree of molecular orientation may be induced both axially and circumferentially when processing a polymer-solvent mixture. It is believed that a higher degree orientation can be induced using the present embodiments than in conventional melt phase extrusion that is done in the absence of a solvent. Similarly, a higher degree of orientation can be induced compared to radial or axial deformation of a formed tube or sheet that does not include a solvent.

As indicated above, molecular weight degradation is a problem in melt phase extrusion of UHMW polymers. Thus, the method of the invention allows for forming a polymeric part to be used in fabricating an implantable medical device composed of relatively high molecular weight polymers, such as UHMW polymers. Using the embodiments of the methods described herein, UHMW polymeric parts can be extruded without significant molecular weight degradation or without any molecular weight degradation. The polymeric parts that may be formed using this invention include, but are not limited to, fibers, tubes, and sheets of various shapes.

Certain embodiments of a method of manufacturing an implantable medical device may include disposing a polymer fluid comprising a solvent and a matrix polymer into a forming apparatus for forming a polymeric part. The matrix polymer may be a relatively high molecular weight polymer, such as an UHMW polymer. The polymer fluid within the forming apparatus may be a gel solution when the matrix polymer in the polymer fluid is a relatively high molecular weight polymer fluid, such as an UHMW polymer.

As indicated above, the temperature within the apparatus may be at a temperature at which there is no or substantially no molecular weight degradation of the matrix polymer in the fluid. In one embodiment, such a temperature may be less than a melting temperature of the matrix polymer. In another embodiment, such a temperature is at or about room temperature. The method may further include cooling or quenching a formed polymeric part, upon removal from the apparatus.

Figure 3:
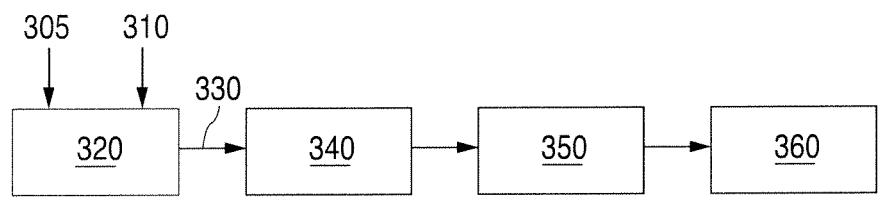
FIG. 3 depicts a method of manufacturing an implantable medical device according to one embodiment of the invention.

FIG. 3 depicts a schematic representation 300 of a method of manufacturing an implantable medical device according to one embodiment of the invention. A polymer 305 and a solvent 310 can be disposed into a mixing apparatus 320 to uniformly or substantially uniformly mix the polymer and solvent to form a polymer-solvent mixture, or polymer fluid 330. Other materials such as particles, active agent, etc. can be introduced into the mixing apparatus 320.

Polymer fluid 330 is then disposed into a forming apparatus 340. Forming apparatus 340 can be, for example, an injection molding apparatus or an extruder. Representative examples of forming apparatuses for the present invention may include, but are not limited to, single screw extruders, intermeshing co-rotating and counter-rotating twin-screw extruders, and other multiple screw masticating extruders. As polymer fluid 330 is conveyed through forming apparatus 340, at least some of the solvent may be vaporized and removed from the forming apparatus 340. The fluid can then be conveyed through a die 350 to form a polymeric part.

In one embodiment, the temperature of the polymer fluid in the forming apparatus is at a temperature at which there is no or substantially no molecular weight degradation of the matrix polymer in the fluid. For example, the temperature of the forming apparatus 340 can be at a temperature below a Tm of the polymer. In this embodiment, the forming apparatus 340 advantageously does not have to be configured to melt the polymer. In certain embodiments, the temperature of the polymer fluid in the apparatus 340 can be at or about room temperature. Thus, the method of the invention advantageously provides a relatively low processing temperature, thereby substantially reducing the molecular weight degradation of the polymer in the forming apparatus 340. In fact, in one embodiment, after forming the polymeric part from the polymer fluid, the average molecular weight of the matrix polymer is greater than about 50%, 70%, 90%, 95%, 99%, or more narrowly, 99.9% compared to a molecular weight of the matrix polymer before formation. In another embodiment, there is no degradation of the polymeric part during formation.

As discussed above, molecular weight degradation is especially a problem with UHMW polymers at higher temperatures. Thus, the method of the invention enables processing of the polymer via gel phase extrusion at a lower temperature, thereby enabling fabrication of implantable medical devices from UHMW polymers.

In some embodiments, the polymeric part prior to cooling may include the polymer and all or substantially all of the solvent disposed in the polymer fluid. In one embodiment, the polymeric part prior to cooling may include at least about 10%, 30%, 50%, 80%, or more narrowly 99% of the solvent present in the polymer fluid. In another embodiment, concentration of the solvent in the polymeric part prior to cooling is the same or substantially the same as the polymer fluid. In another embodiment, the concentration of the solvent in the polymeric part prior to cooling is at least about 10%, 30%, 50%, 80%, or more narrowly 99% of the concentration of the solvent in the polymer fluid. In other embodiments, the concentration of the solvent in polymeric part prior to cooling is the same or substantially the same as the concentration of the solvent in the polymer fluid.

The method of the invention further includes cooling the formed polymeric part in a cooling apparatus 360, upon removal from die 350. In some embodiments, the cooled polymeric part may include the polymer and all or substantially all of the solvent in the polymer fluid. In one embodiment, the cooled polymeric part may include at least about 10%, 30%, 50%, 80%, or more narrowly 99% of the solvent present in the polymer fluid. In another embodiment, the concentration of the solvent in the cooled polymeric part may be the same or substantially the same as the polymer fluid. In other embodiments, the concentration of the solvent in the cooled polymeric part is at least about 10%, 30%, 50%, 80%, or more narrowly 99% of the concentration of the solvent in the polymer fluid. In other embodiments, the concentration of the solvent in the cooled polymeric part is the same or substantially the same as the concentration of the solvent in the polymer fluid. In an embodiment, an implantable medical device may then be fabricated from the cooled polymeric part.

The formed polymeric part can be cooled by contacting the polymeric part with a cooling fluid having a selected temperature. For example, the formed polymeric part can be cooled in a quench bath to form a cooled polymeric part. Alternatively, the formed polymeric part may be cooled by air or some other gas at a selected temperature. The cooling fluid in the cooling apparatus 360 may allow at least a portion of the solvent to diffuse out of the formed polymeric part without dissolving or significantly dissolving the polymer. Some examples of cooling fluids include, but are not limited to, isopropyl alcohol, chloroform, acetone, water, and any mixtures thereof in any proportion. Other cooling fluids are also contemplated for use in cooling the formed polymeric part upon removal from the die 350.

In one embodiment, the temperature at which the formed polymeric part is cooled can be a temperature such that at least a portion of the cooled polymeric part includes a gel. A "gel" refers a solid, jellylike material that includes a mixture of a relatively high molecular weight polymer or ultra high molecular weight polymer and solvent. A polymeric part, such as a tube, sheet, or fiber, is capable of maintaining its shape even through it contains a substantial amount of solvent. For example, the formed polymeric part can be cooled at a temperature at or near an ambient temperature, e.g., 25° C. The formed polymeric part can also be cooled at a temperature below ambient temperature.

In some embodiments, the cooled polymeric part may include the polymer and a substantial portion of the solvent from the polymer fluid upon removal from the forming apparatus 340 and die 350. In one embodiment, the molecular weight of the polymer and the relative concentration of the polymer and the solvent in the polymer fluid can be such that a polymeric part substantially maintains its shape upon removal from the forming apparatus 340. For example, the molecular weight of the polymer in the solvent may be greater than 500,000, greater than 700,000, greater than 800,000, or more narrowly, greater than 1 million. The concentration of the matrix polymer in the polymer fluid can be between about 0.1 w/w to about 20% w/w.

In one embodiment, most of the solvent that remains disposed in the cooled polymeric part may be in an inner portion of the polymeric part while the outer portion may have less dissolved solvent. As a result, the outer portion of the polymeric part, such as a polymeric tube, may be firmer, thus providing structural integrity to the cooled polymeric part, while the inner portion may be in a softer, gel-like state.

As indicated above, mixing a solvent with the polymer effectively lowers the glass transition temperature of the polymer. The polymer chains in the polymer fluid have segmental mobility analogous to that of the polymer above its glass transition temperature and melting temperature. The increased segmental mobility advantageously allows a reduced processing temperature.

As mentioned above, a polymeric part, such as a tube or sheet, made from relatively high molecular weight polymer fluid, such as UHMW polymers, is capable of maintaining structural integrity while retaining a substantial amount of solvent. In contrast, in the extrusion of a polymer fluid including a low molecular weight polymer, all or substantially all of the solvent has to be extracted from the polymer fluid so that a formed polymeric part can maintain its structural integrity. Drawing of such a formed tube or sheet or radially expanding of such a tube is generally performed at a temperature greater than the Tg of the polymer. Structural integrity of a formed polymeric part cannot be maintained without removal of all or substantially all of the solvent. Therefore, higher temperatures are required for the polymer in the polymeric part to have segmental mobility.

In contrast, the present invention provides for a requirement for extracting less solvent to maintain the shape of the polymeric part because the high molecular weight polymer maintains the structural integrity of the polymeric part. The gel-like inner portion of the polymeric part due to the presence of a significant amount of solvent within such portion facilitates axial and circumferential deformation at lower temperatures. The gel-like portion has an effectively lower Tg than polymer with little or no solvent. The reduced Tg of the gel-like portion facilitates inducing molecular orientation during axial and circumferential deformation.

In one embodiment, the method further includes axially deforming or drawing the cooled polymeric part, such as a tube or sheet. The invention advantageously may allow for axial deformation or drawing of the cooled polymeric part to a desired length. Because a substantial amount of solvent may remain disposed in the polymeric part upon removal from the forming apparatus 340, the polymeric part can be drawn to higher draw ratios than a polymeric part with little or no solvent. A higher draw ratio can result in higher induced axial molecular orientation and higher induced axial strength. In one embodiment, the polymeric part may be drawn to a length of at least about 5, 10, 15, or 20 times the original length. In another embodiment, the cooled polymer part may be axially deformed or drawn during and/or after removal of all or substantially all solvent from the cooled polymeric part.

A tube, sheet, or fiber, for example, may be drawn using methods and devices know to persons of skill in the art. For example, a pulling device may include a conveyor assembly that supports and sizes a tube, sheet, or fiber. It should also be understood by those skilled in the art that the expanded or drawn polymeric part can be cooled during and/or after drawing the polymeric part. Furthermore, the drawing speed may also be controlled to obtain a desired degree of induced axial orientation. As the drawing speed is increased, the degree of induced axial molecular orientation decreases.

Certain embodiments of the invention of forming a polymeric tube can further include radially expanding the cooled tube about a cylindrical axis of the tube before removing all or substantially all solvent from the cooled polymeric part. As discussed above, radial expansion of the polymeric tube can induce circumferential molecular orientation which can increase circumferential strength and modulus or rigidity in the polymer tube. In some embodiments, the tube may be radially expanded during and/or after removal of all or substantially all solvent from the cooled polymeric part. The tube may be expanded radially by application of radial pressure. For example, the tube may be expanded by blow molding. In blow molding, a tube may be disposed into conduit or mold. A gas at a selected pressure is then conveyed into the tube to expand the tube. The mold places an upper limit on the radial expansion of the tube. An implantable medical device can then be fabricated from the expanded tube. It should also be understood by those skilled in the art that the tube can be radially expanded prior to drawing or axially expanding the tube.

The induced axial and circumferential strength provides for an implantable medical device having thinner walls that also has sufficient circumferential strength for supporting a bodily lumen. A thin-walled device is also more longitudinally flexible as compared to polymer stents with thick walls and metal stents. Further, an implantable medical device that is made using the method of the invention may experience lower recoil after being implanted into a bodily lumen due to the higher circumferential strength.

Additionally, certain embodiments of the method may include removing the solvent from the polymeric part after the polymeric part has exited forming apparatus 340, after the polymeric part has exited die 350, or after the polymeric part has been cooled by cooling or quenching apparatus 360. For example, the residual solvent may be removed from the polymeric part by drying the polymeric part. The polymeric part may be allowed to heat set during the drying process. The polymeric part may be dried by air drying, blowing an inert gas on the polymeric part, or in an oven. "Heat setting" refers to maintaining the polymeric part in a selected configuration for a period of time at an elevated temperature.

In certain embodiments, the method may also include fabricating an implantable medical device from the polymer part after or during removal of all or substantially all of the solvent. For example, a stent, as such as that depicted in FIG. 1, may be fabricated by forming a pattern on a cooled tube that includes a plurality of interconnecting structural elements. Alternatively, stent may be formed from a sheet by rolling and bonding the sheet to form a tube.

In some embodiments, the pattern of the stent can be formed by cutting a pattern on a cooled tube. For example, the pattern can be cut on the tube with a laser, such as with an excimer, carbon dioxide, or YAG laser. In other embodiments, chemical etching may be used to form a pattern on the tube. A laser cutting technique that minimizes a size of a heat affected zone is especially advantageous. The heat affected zone refers to a region of a target material affected by the heat of the laser. Heat from the laser can melt some portion of the polymer in the heat affected zone. The molecular orientation induced by applied stress and the corresponding favorable change in mechanical properties can be reduced by the heat from the laser.

Additionally, as described above, a stent may be fabricated from formed fibers. For example, a stent can be formed from a woven fiber structure. Fibers can also be mixed, dispersed, or embedded into a polymer matrix of a device such as a stent.

The stent fabricated using the method of the invention can have high crystallinity, high strength, and high molecular weight, thereby providing more resistance to physical aging and creep.

Further embodiments of the invention may also include forming a stent from a polymer fluid, as described above, which involves inducing desired molecular orientation with electric charges in a polymer fluid. In certain embodiments of the invention, a charge may be induced in a polymer fluid within a forming apparatus. The polymer fluid may include a relatively high molecular weight polymer, as described above. In one embodiment, a polymer fluid may be charged by inducing a positive and a negative electric charge at selected positions along an axis of the forming apparatus. For example, positive and negative charges may be induced by electrodes positioned at or adjacent to the entry and exit of a forming apparatus, respectively.

Figure 4A:
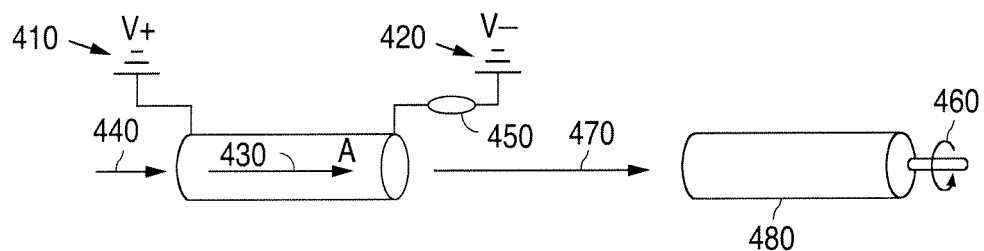
FIG. 4A depicts a method of manufacturing an implantable medical device that includes inducing a charge on a forming apparatus.

FIG. 4A depicts a positive electrode 410 on the entry end and a negative electrode 420 at the exit end of a forming apparatus 430 which establishes a static electric field in the polymer fluid. Alternatively, the negative charge can be induced on the entry end and the positive charge can be induced at the exit end of forming apparatus 430. A power supply 450 can provide voltage and current to charge a polymer fluid 440 that is introduced into forming apparatus 430. The polymer molecules are polarized by the high voltage.

In one embodiment, relatively high voltage and relatively low current are supplied by the power supply. For example, the voltage may be in the range of 5-30 kV. The voltage may vary as known by those skilled in the art depending on the desired fiber diameter. As those skilled in the art understand, the voltage may vary depending on the solution viscosity, the distance between the spraying device and electrode, fiber diameter, etc.

Forming apparatus 430 may correspond to, for example, an extruder, die, or both. Negative and positive electrodes may be positioned along an axis of the extruder, die, or both. Power supply 450 provides high voltage and low current which charges the polymer fluid. Thus, polymer chains in the polymer fluid are oriented along an axis of forming apparatus 430 by the charges induced by electrodes.

Figure 4B:
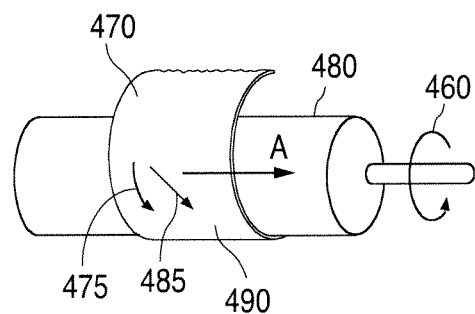
FIG. 4B depicts a rotation drum.

In one embodiment, forming apparatus 430 is configured to form a film or sheet 470. Sheet 470 has induced molecular orientation along an axis of forming apparatus 430. In some embodiments, as depicted in FIG. 4A-B, polymeric sheet 470 that exits forming apparatus 430 is deposited on a surface of a tubular member such as rotation drum 480. A polymeric tube 490 is formed on rotation drum 480 as rotation drum rotates as shown by an arrow 460. The solvent evaporation rate may be controlled so that sheet may be coated over rotation drum 480 with most or all of solvent being removed. The solvent evaporation rate may be controlled, for example, by adjusting the temperature of sheet 470.

Sheet 470 may be deposited on the rotation drum 480 so that the direction of induced orientation in tube 490 is along a circumferential direction of rotation drum 430, as shown by an arrow 475. In general, polymeric sheet 470 may be deposited on rotation drum 480 so that the direction of induced orientation is in any desired direction. The induced orientation may be along longitudinal axis A of rotation drum 480 or between a circumferential direction and longitudinal axis A, as shown by an arrow 485.

In one embodiment, a multilayer tube may be formed by depositing a sheet from the forming apparatus above a sheet already deposited on rotation drum 480. The layers may have the same or different induced polymer orientations. For example, induced orientation of the layers may alternate between a circumferential direction and longitudinal direction.

In some embodiments, a composite polymeric tube may be formed. For example, particles such as fibers (e.g., nanofibers) can be incorporated into the polymeric tubes or sheets prior to fabrication of the implantable medical device. In one embodiment, the particles may be mixed with the polymer fluid in the forming apparatus.

Figure 5:
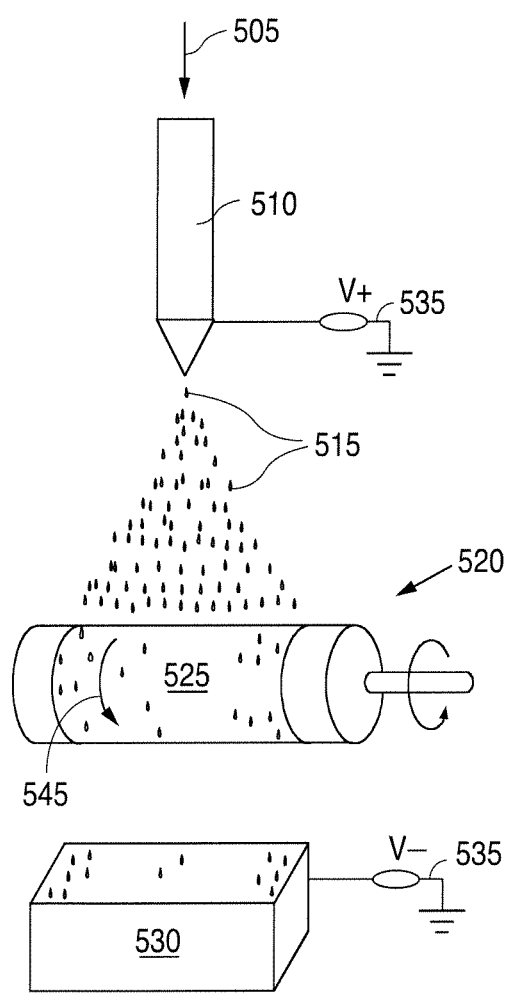
FIG. 5 depicts an electron spinning apparatus.

In one embodiment, as depicted in FIG. 5, an electron spinning process can be used to incorporate particles into or onto a preformed tube 525 which has been formed from a polymer fluid according to the method described above. In other embodiments, particles may be deposited directly on a rotation drum to form a polymer fiber tube. The particles formed from electron spinning may include fibers having a width between 10 to 10000 nanometers, or more narrowly 10 to 500 nanometers. The fibers formed by electron spinning may be deposited on tube 525 or rotation drum 520 so that they are aligned along the circumferential direction which provides circumferential strength in addition to the alignment of the polymer chains in preformed tube 525.

In electron spinning, a voltage from a voltage supply 535 is supplied to a spraying device 510 and to a ground collection plate 530. The rotation drum 520 can also be charged by electrodes or can be grounded by ground collection plate 530. Spraying device 510 is configured to spray polymer fluid 505 to form fibers. The feeding rate can be, for example, 1 ml/hour. Spraying device 510 can include a syringe fitted to a needle with a tip. A thin film of fluid is pulled off the surface of the tip of the needle to form a positively charged jet of fluid 515 that is accelerated towards grounded rotation drum 520 due to high potential or electrostatic charge and the force of gravity. High voltage can be applied to the needle using a high voltage power supply 535.

Fluid jet 515 forms fibers as solvent evaporates. All or a substantial portion of the solvent may evaporate before the fibers are deposited as a thin layer on tube 525 or grounded rotation drum 520. It is believed that the polymer chains in the fluid jet 515 are disentangled and form a highly oriented structure along a fiber axis. The highly oriented fiber tends to stabilize after the fiber solidifies. Grounded collection plate 530 can be located at a distance from the needle tip of the spraying device 510 so as to attract the charged fibers toward grounded rotation drum 520.

Fibers formed from fluid jet 515 may be deposited on preformed tube 525 on rotation drum 520. The deposited fibers can form a layer of fibers over preformed tube 525. Alternatively, the fibers may be deposited directly on to rotation drum 520 without having a preformed tube to form a polymer fiber tube. The deposited fibers can then be dried under vacuum at room temperature.

Fibers formed over preformed tube 525 or over rotation drum 520 may be aligned along the circumferential direction resulting from the motion of the rotation drum 520. The high degree of orientation in the circumferential direction 545 increases circumferential strength of the polymeric tube formed on the rotation drum 520.

In one embodiment, polymer fluid 505 includes a polymer having a molecular weight above 500,000, and more narrowly above 1,000,000. It should be understood by those skilled in the art that the formed polymeric tube of fibers can be layered with other polymeric material if desired. The formed polymeric tube may then be used to fabricate an implantable medical device. For example, a stent may be formed from the cooled tube by forming a stent from the cooled tube by forming a pattern of interconnecting structural elements.

The ground collection plate 530 can be located at a fixed distance of about 10 cm underneath the spray tip of the spray device 510. The ground collection plate 530 can be made up of any material which allows voltage to run through the ground collection plate 530. For example, the ground collection plate 530 can be made of aluminum foil. Because of the charge on the ground collection plate 530, the fluid is drawn toward a grounded collecting plate 530 toward rotation drum 520.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of manufacturing a stent, the method comprising:
   a. dissolving a matrix polymer having a number average molecular weight of at least 100,000 Da in a first solvent at a concentration such that a gel is formed; wherein
      the matrix polymer is selected from the group consisting of Poly(D,L-lactide); poly(L-lactide); Poly(L-lactide-co-glycolide); poly(D,L-lactide-co-glycolide); chitin; chitosan; any copolymers thereof, and any mixtures thereof in any proportion;
   b. extruding the gel through an extrusion apparatus to form a tube or a sheet;
   c quenching the formed tube or sheet in a second solvent that does not dissolve the matrix polymer but which allows the first solvent to diffuse out of the polymer;
   d. radially expanding and axially orienting the formed tube or biaxially orienting the formed sheet;
   e. drying the tube or sheet; and
   f. forming the stent from the dried tube or sheet.

2. The method according to claim 1, wherein the tube is axially oriented by deforming it to at least about 20 times its initial length.

3. The method according to claim 1, wherein the matrix polymer has a number average molecular weight of at least 500,000 Da.

4. The method according to claim 1, wherein the matrix polymer has a number average molecular weight of at least 1,000,000.

5. The method according to claim 1, wherein the concentration of the polymer in the solvent is about 0.1 percent (w/w) to about 20% percent (w/w).

6. The method according to claim 1, wherein the gel in the extrusion apparatus is at a temperature at which there is no or substantially no molecular weight degradation.

7. The method according to claim 6, wherein the temperature of the gel in the extrusion apparatus is about room temperature.

8. The method according to claim 1, wherein after forming the tube or sheet from the polymer gel and drying the tube or sheet, the average molecular weight of the matrix polymer is greater than 90% of its molecular weight prior to extrusion.

9. A method of manufacturing a stent, the method comprising:
   a. disposing a polymer fluid comprising a solvent and a matrix polymer into a forming apparatus;
   b. inducing a charge in the polymer fluid, wherein the charge induces orientation of polymer chains in the polymer fluid;
   c. forming a gelatinous polymeric sheet with the induced orientation from the charged polymer fluid;
   d. depositing the polymeric sheet onto a rotating cylindrical member to form a polymeric tube with the induced orientation over the rotating cylindrical member; and
   e. fabricating the stent from the polymeric tube.

10. The method according to claim 9, wherein the forming apparatus is selected from the group consisting of a die, an extruder, or a combination thereof.

11. The method according to claim 9, wherein a temperature of the polymer fluid in the forming apparatus is at or about room temperature.

12. The method according to claim 9, wherein the polymeric tube is formed such that it comprises the induced orientation along a selected direction.

13. The method according to claim 9, wherein the polymeric sheet is deposited so that the polymeric tube comprises multiple layers.

14. The method according to claim 9, wherein the number average molecular weight of the polymer is at least 100,000.

15. The method according to claim 9, wherein a relative concentration of the polymer and the solvent in the polymer fluid are such that the polymeric sheet substantially maintains its shape upon removal from the apparatus.

16. The method according to claim 9, further comprising depositing fibers over the polymeric tube to form a cylindrical fiber layer over the polymeric tube.

* * * * *